(12) United States Patent
Abood

(10) Patent No.: US 12,226,230 B1
(45) Date of Patent: *Feb. 18, 2025

(54) CARE GIVER DISPLAY SURGICAL CAP TO CONTROL PATIENT BODY TEMPERATURE

(71) Applicant: David G. Abood, Rocky River, OH (US)

(72) Inventor: David G. Abood, Rocky River, OH (US)

(*) Notice: Subject to any disclaimer, the term of this patent is extended or adjusted under 35 U.S.C. 154(b) by 166 days.

This patent is subject to a terminal disclaimer.

(21) Appl. No.: 18/102,277

(22) Filed: Jan. 27, 2023

Related U.S. Application Data

(63) Continuation-in-part of application No. 17/104,040, filed on Nov. 25, 2020, now Pat. No. 11,980,246, which is a continuation-in-part of application No. 16/242,295, filed on Jan. 8, 2019, now Pat. No. 11,857,019, which is a continuation-in-part of application No. 15/872,095, filed on Jan. 16, 2018, now Pat. No. 11,528,950, which is a continuation-in-part of application No. 14/850,940, filed on Sep. 10, 2015, now abandoned, which is a continuation-in-part of application No. 13/692,060, filed on Dec. 3, 2012, now Pat. No. 11,545,052, which is a continuation-in-part of application No. 12/649,887, filed on Dec. 30, 2009, now Pat. No. 10,219,568.

(60) Provisional application No. 62/447,424, filed on Jan. 17, 2017, provisional application No. 62/048,684, filed on Sep. 10, 2014.

(51) Int. Cl.
*A61B 5/00* (2006.01)
*A42B 1/017* (2021.01)
*A61B 5/0205* (2006.01)

(52) U.S. Cl.
CPC ............ *A61B 5/6803* (2013.01); *A42B 1/017* (2021.01); *A61B 5/02055* (2013.01); *A61B 5/7445* (2013.01)

(58) Field of Classification Search
CPC ...... A61B 5/6803; A41D 31/06; A42B 1/045; A42B 1/249; A42B 1/112
See application file for complete search history.

(56) References Cited

U.S. PATENT DOCUMENTS

| 430,003 | A | * | 6/1890 | De Lacy | ................ A42B 1/012 2/209.5 |
| 1,426,402 | A | * | 8/1922 | Moore | ...................... B63C 9/15 2/200.2 |

(Continued)

*Primary Examiner* — Richale L Quinn
(74) *Attorney, Agent, or Firm* — Gugliotta & Gugliotta, LPA

(57) ABSTRACT

A system and method for maintaining a patient's body temperature during and after surgical exposure is provided. A surgical, insulative cap both aids in maintaining the patient's core body temperature at an euthermic range and further incorporates a graphic display panel for providing a remote caregiver informational interface. Vital signs sensors may therefor communicate, either directly or remotely, to said informational interface and allow access to vital signs information to the caregiver in a convenient manner that does not require diversion of attention from the patient in order to monitor. Medical information can be communicated in a visual or audible manner, including alerts, status or patient care instructions.

8 Claims, 2 Drawing Sheets

(56) References Cited

U.S. PATENT DOCUMENTS

| | | | | |
|---|---|---|---|---|
| 1,819,558 A * | 8/1931 | Husman | A42B 1/12 | D2/880 |
| 2,193,271 A * | 3/1940 | Cowherd | A42B 1/049 | D24/189 |
| 2,417,323 A * | 3/1947 | Richards | A42B 1/12 | D2/867 |
| 2,644,949 A * | 7/1953 | Greenberg | A42B 1/0189 | 2/172 |
| 2,726,398 A * | 12/1955 | Cooper | A42B 1/12 | 2/174 |
| 2,885,683 A * | 5/1959 | Lipkin | A42B 1/0186 | 2/172 |
| 3,296,582 A * | 1/1967 | Ide | G10K 11/002 | 181/175 |
| 3,321,774 A * | 5/1967 | Tames | A42B 1/012 | 2/181 |
| 3,463,161 A * | 8/1969 | Stella | B65D 81/3895 | 126/400 |
| 3,512,181 A * | 5/1970 | Osborne | A42B 1/012 | D2/881 |
| 3,699,590 A * | 10/1972 | Webber | A41D 31/26 | 361/220 |
| 3,872,516 A * | 3/1975 | Bird | A42B 1/045 | 2/202 |
| 4,017,908 A * | 4/1977 | Murnane | B63C 9/20 | 2/114 |
| 4,061,898 A * | 12/1977 | Murray | A42B 1/008 | 219/549 |
| 4,120,294 A * | 10/1978 | Wolfe | A61B 5/02438 | 600/523 |
| D258,696 S * | 3/1981 | Evans | D2/868 | |
| D268,696 S * | 4/1983 | Bowen | D24/207 | |
| 4,382,446 A * | 5/1983 | Truelock | A61F 7/03 | 607/110 |
| D269,304 S * | 6/1983 | Schonwetter | D29/102 | |
| 4,425,916 A * | 1/1984 | Bowen | A61F 7/106 | 607/110 |
| 4,459,471 A * | 7/1984 | Hulett | H05B 3/342 | 219/549 |
| D276,651 S * | 12/1984 | Fischer | D24/206 | |
| 4,491,985 A * | 1/1985 | Dalton | A42B 1/041 | 2/209.12 |
| 4,552,149 A * | 11/1985 | Tatsuki | A61F 7/10 | 607/110 |
| 4,573,217 A * | 3/1986 | Reed | A62B 17/04 | 2/205 |
| 4,951,319 A * | 8/1990 | Phillips, Jr. | A42C 5/04 | 2/209.12 |
| 4,998,296 A * | 3/1991 | Stames | A41D 31/102 | 2/84 |
| 5,253,368 A * | 10/1993 | Blake | B43K 29/00 | 40/329 |
| RE35,290 E * | 7/1996 | Druskoczi | A61F 5/055 | 602/18 |
| 5,594,956 A * | 1/1997 | Barrientos | A42B 1/22 | 2/172 |
| 5,603,728 A * | 2/1997 | Pachys | A61F 7/02 | 607/104 |
| 5,628,065 A * | 5/1997 | Austin | A42B 1/048 | 2/5 |
| 5,850,636 A * | 12/1998 | Reuven | A42B 1/008 | 2/200.1 |
| 5,884,760 A * | 3/1999 | Carpenter | A62B 3/00 | 2/88 |
| D417,282 S * | 11/1999 | Allen | D24/207 | |
| 6,014,776 A * | 1/2000 | DeVinzio | A42B 1/041 | 2/172 |
| 6,247,181 B1 * | 6/2001 | Hirsch | A42B 1/041 | 2/412 |
| 6,360,376 B1 * | 3/2002 | Carrington | A42B 3/00 | 2/412 |
| 6,427,685 B1 * | 8/2002 | Ray, II | G09B 23/288 | 434/262 |
| D473,365 S * | 4/2003 | Bias | D2/867 | |
| 6,557,179 B1 * | 5/2003 | Reuven | A42B 1/008 | 2/209 |
| 6,625,817 B2 * | 9/2003 | Wasmuth | A42B 1/008 | 2/174 |
| 6,751,805 B1 * | 6/2004 | Austion | A41D 27/08 | 2/94 |
| 6,820,283 B2 * | 11/2004 | Graneto, III | A45D 19/14 | 2/171.2 |
| 6,918,138 B2 * | 7/2005 | Donovan | A45D 19/14 | 2/204 |
| 6,966,068 B2 * | 11/2005 | Johnson | A42B 1/12 | 2/200.2 |
| 7,310,553 B2 * | 12/2007 | Freeman | A61N 1/3987 | 601/41 |
| 7,401,365 B2 * | 7/2008 | Neal | A42B 3/0406 | 40/329 |
| D584,000 S * | 12/2008 | Saluan | D29/106 | |
| 7,744,640 B1 * | 6/2010 | Faries, Jr. | A61F 7/007 | 607/108 |
| 7,930,768 B1 * | 4/2011 | Tyler | A42B 1/041 | 2/205 |
| 8,257,274 B2 * | 9/2012 | Medina | A61B 5/01 | 600/549 |
| 8,262,601 B2 * | 9/2012 | Cumming | A61F 13/12 | 602/14 |
| 8,744,573 B2 * | 6/2014 | Freeman | A61H 31/004 | 600/509 |
| 8,781,548 B2 * | 7/2014 | Besko | A61B 5/6806 | 600/324 |
| D714,666 S * | 10/2014 | Abood | D10/57 | |
| 9,149,393 B2 * | 10/2015 | Cumming | A61F 13/12 | |
| 9,578,914 B2 * | 2/2017 | Fierro | A63B 33/00 | |
| 9,730,479 B2 * | 8/2017 | Lewis | A41D 3/00 | |
| 11,545,052 B1 * | 1/2023 | Abood | A42B 1/012 | |
| 2001/0047140 A1 * | 11/2001 | Freeman | A61N 1/0492 | 601/41 |
| 2003/0066120 A1 * | 4/2003 | Tremblay-Lutter | A41D 19/001 | 2/164 |
| 2004/0116822 A1 * | 6/2004 | Lindsey | G01K 13/20 | 374/E1.004 |
| 2004/0221370 A1 * | 11/2004 | Hannula | A61B 5/14552 | 2/181 |
| 2005/0183182 A1 * | 8/2005 | Keenan | A61B 90/04 | 2/114 |
| 2005/0278824 A1 * | 12/2005 | Gadot | A41D 27/02 | 2/108 |
| 2007/0078324 A1 * | 4/2007 | Wijisiriwardana | A61B 5/389 | 600/389 |
| 2007/0157358 A1 * | 7/2007 | Sharon | G09F 3/02 | 2/69 |
| 2008/0146958 A1 * | 6/2008 | Guillory | A61B 5/4094 | 600/544 |
| 2009/0144882 A1 * | 6/2009 | Neri | A42B 1/24 | 40/329 |
| 2009/0253996 A1 * | 10/2009 | Lee | A61B 5/165 | 600/544 |
| 2010/0024091 A1 * | 2/2010 | Mehtab | A42B 1/206 | 2/244 |
| 2010/0076282 A1 * | 3/2010 | Sandmore | A61B 5/6843 | 600/587 |
| 2010/0076337 A1 * | 3/2010 | Medina | A61B 5/6804 | 2/171.2 |
| 2010/0249554 A1 * | 9/2010 | McKenna | A61B 5/1455 | 600/324 |
| 2010/0249557 A1 * | 9/2010 | Besko | A61B 5/6814 | 600/340 |
| 2011/0092935 A1 * | 4/2011 | Hann | A61F 13/47272 | 604/360 |
| 2011/0093296 A1 * | 4/2011 | Klink | G16H 10/65 | 705/3 |
| 2012/0144555 A1 * | 6/2012 | Panicali | A42B 1/008 | 2/171.2 |

(56) References Cited

U.S. PATENT DOCUMENTS

| | | | |
|---|---|---|---|
| 2012/0204306 A1* | 8/2012 | Fierro | A42B 1/12 2/68 |
| 2014/0026284 A1* | 1/2014 | Yates | A63B 33/00 2/67 |
| 2014/0338099 A1* | 11/2014 | Marscellas | A42B 1/012 2/209.13 |
| 2015/0228205 A1* | 8/2015 | Koskimaki | A61B 5/742 128/202.28 |
| 2018/0169358 A1* | 6/2018 | Jackson | A61M 16/0048 |
| 2019/0046114 A1* | 2/2019 | Bogdanovich | A61B 5/6804 |
| 2020/0029900 A1* | 1/2020 | Bogdanovich | A61B 5/6804 |
| 2020/0054116 A1* | 2/2020 | Sola | G01F 23/0007 |

\* cited by examiner

CARE GIVER DISPLAY SURGICAL CAP TO CONTROL PATIENT BODY TEMPERATURE

RELATED APPLICATIONS

The present application is a Continuation in Part of U.S. Ser. No. 17/104,040, filed on Nov. 25, 2020, which was a continuation in part of U.S. Ser. No. 15/872,095, filed on Jan. 16, 2018, and now U.S. Pat. No. 11,528,950. Additional applications of related continuity are further disclosed as part of the Application Data Sheet filed pursuant to 37 C.F.R. § 1.76. All Related Applications are incorporated by reference as if fully rewritten herein.

BACKGROUND OF THE INVENTION

1. Field of the Invention

The present invention relates generally to a device and a method that maintains a patient's body temperature during surgical procedures and, more specifically, to a surgical, insulative cap that both aids in maintaining the patient's core body temperature at an euthermic range and further incorporates a graphic display panel for providing a caregiver informational interface.

2. Description of the Related Art

The vast majority of patients that undergo anesthesia experience some level of hypothermia. The decrease in temperature is variable, but it worsens in the procedures that involve larger and lengthier surgical exposures. The state of relative hypothermia can significantly and adversely affect a patient, especially during the perioperative and the postoperative periods. However, due to physical and logistical limitations, it is difficult to continuously monitor a surgical patient's body temperature at most times in the perioperative, and postoperative periods.

The present invention teaches a surgical, insulative cap that is designed both to contour a patient's head and ears and to maintain its position during surgery in combination with an interface for displaying the output of biometric sensors that can provide continuous, accurate standard vital body sign parameters such as body temperature, but can also include sensors for other biometric data such as body temperature heart rhythm, heart rate, breathing activity, SpO2, etc. sufficient to detect malignant hyperthermia or hypothermia as well as other deleterious perioperative, and postoperative conditions. Further, the display screen may be combined with a number of products and made interactive in order to provide alerts, status or patient care instructions in visual or audible manner.

SUMMARY OF THE INVENTION

It is an object of the present invention to provide a flexible and a disposable surgical cap that is worn by patients during surgical procedures.

It is an object of the present invention to reduce the risks to patients, especially to the frail patients at higher risks for developing hypotension, tachycardia and the other conditions related to surgical hypothermia.

It is an object that the present cap is comprised of an insulative material that is both stretchable and flexible to provide a means for the cap to follow the contour of a head.

It is an object that the present surgical cap is constructed to minimize exposures to fibrous materials and, as such, to remove any habitat for bacterial growth.

It is an object of the present cap to prevent excessive airflow between the cap material and a patient's head by eliminating the large air gap between the two. This object is accomplished by minimizing the amount of surface area covered by the cap while also retaining the cap on the patient's head.

It is an object of the present invention to provide such a surgical cap that incorporates a display element for providing a caregiver interface for the sensors that are monitoring the functions of vital body systems.

It is a further object of the present invention to provide visual and/or audible interactive prompts for altering adverse changes in core vitals or alerting caregivers as to next steps for patient care.

It is envisioned that the present surgical cap includes an insulative inner portion and a shell fabricated from the materials sold under the trademarks Thermalite®, Thinsulate® or Outlast®. More specifically, the cap includes a ceramic fiber material, a commercially synthetic material having fibers that contain a plurality of microencapsulated and paraffinic hydrocarbons (hereinafter a "phase change material") and a synthetic microfiber having a composition approximating 65% olefin and 35% polyester. The cap extends over a greater portion of a patient's forehead, over the patient's ears and behind the head to reach as far as the top of the cervical spine. According to one aspect of the invention, monitoring sensors may be integrated directly into the cap in contact with the patient's head in order to facilitate acquisition and display of standard vital body sign parameters. According to yet another aspect of the invention, the cap can be in informational communication, either audio or visual, with various other monitoring sensors placed about the patient for acquisition of standard body sign parameters. In either aspect, any number of standard body sign parameters may be acquired, such as ECG, heart rate, breathing, oxygen saturation (SpO2), temperature, or the like. Further, advanced measurements may additionally be integrated merely with the inclusion of appropriate biometric sensors and analyzers.

It is envisioned that the present surgical cap includes a caregiver interface in the form of a display screen positioned at the front of the cap in alignment with the patient's forehead. The present invention provides for utilization in an environment beyond the operating room. The location and operation of such an interface display screen allows doctors, nurses, EMT's or others to easily access the information output of selected vital body sign sensors in a manner that both travels with the patient as well as eliminates the need for a caregiver to divert attention from patient care activities.

It is an object of the present invention to provide a surgical, insulative cap that both aids in maintaining the patient's core body temperature at an euthermic range and further incorporates an information display for communication with biometric sensor capacity.

It is a final object of the present invention to provide all of the advantages that the foregoing objects entail. The present invention departs from the current designs to overcome their respective disadvantages. The present invention will maintain its position during and after the repeated times an anesthesiologist manipulates the head's position to access monitor apparatuses. The present invention continues to provide access to the central venous region. The present invention will provide a display for the proper position for viewing information from sensors for acquiring body sign parameters including: body temperature; electrocardiogram (ECG); respiratory rate (RR) and End Tidal Carbon Dioxide (ETCO2); heart rate (HR); oxygen saturation (SpO2); photoplethysmography (PPG); blood glucose (BG); carbon monoxide level (SpCO); blood pressure (BP); and hydration levels (HL).

Additionally, it is envisioned that the use of physical tracking of location or position, such as through GPS or other means, may be incorporated for healthcare, military, industrial and consumer markets.

The present invention may similarly be used for nonsurgical patients with temperature regulatory issues, such as immunocompromised individuals, patients undergoing dialysis, and cancer patients.

Further features of the invention will become apparent in the course of the following description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

Figure 1:
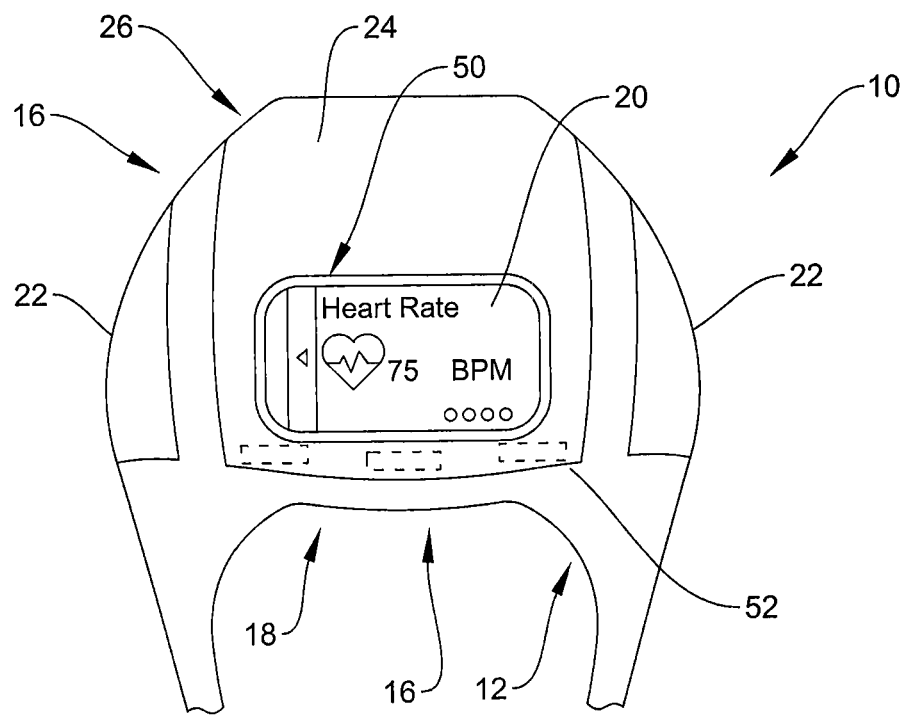
FIG. 1 depicts a front elevational view of a Surgical Cap to Control Patient Body Temperature according to a preferred embodiment of the present invention.

The best mode for carrying out the invention is presented in terms of its preferred embodiment, herein depicted within the Figures. It should be understood that the legal scope of the description is defined by the words of the claims set forth at the end of this patent and that the detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

The best mode for carrying out the invention is presented in terms of its preferred embodiment, herein depicted within the Figures.

1. Detailed Description of the Figures

Referring now to the Figures, a medical sensor and covering unit combination, generally noted as 10, is shown for covering a patient's head for maintaining the head temperature and core body temperature within euthermic range during surgery. The covering unit 10 covers a substantial portion of a patient's head, as will be described in greater detail below, and forms a multi-part shell component having an inner surface 12 adapted for closely fitting the contours of a patient's head so as to prevent open air space between the head and an inner surface. The shell component further has an outer surface 14, and forming an opening 16 circumscribed by a gripping lower edge 18. This gripping lower edge 18 forms a gripping means for gripping to a patient's head in a manner such as to impede said the head covering unit from coming off of the patient's head during surgery.

The cap 10 extends over a greater portion of a patient's forehead, over the patient's ears and behind the head to reach as far as the top of the cervical spine. According to one aspect of the present invention, a functional electronics package in the form of a sensor patch may be incorporated within the cap 10. Such an aspect may utilized a removable patch module 50 that incorporates monitoring sensors 52 accessing an inner surface in a manner taught by the Related Applications, incorporated by reference as if fully rewritten herein. According to a further aspect of the present invention informational communication with remote sensors of an otherwise conventional or remote location affixed to a patient's body that can communicate wirelessly to provide vital signs information. It is envisioned that the present surgical cap includes a caregiver interface in the form of a display screen 20 positioned at the front of the cap in alignment with the patient's forehead. The location and operation of such an interface display screen allows doctors, nurses, EMT's or others 60 to easily access the information output of selected vital body sign sensors 52 in a manner that both travels with the patient as well as eliminates the need for a caregiver to divert attention from patient care activities.

It should be apparent to a person having ordinary skill in the relevant art, in light of the present teachings, that alternate sensor configuration or placement may be provided, and that such modifications are and should be broadly considered within the range of equivalents of the present invention. By way of one example, and not as a limitation, monitoring sensors may be integrated directly into the inner surface 12 of the cap 10 in contact with the patient's head in order to facilitate acquisition of standard vital body sign parameters. By way of another example, and not as a limitation, monitoring sensors 53 may be distributed about and attached to various other parts of the patient's body and be in communication wirelessly with the display 20 on the patient's head in order to facilitate acquisition of standard vital body sign parameters.

In any sub-configuration, the cap 10 is intended maintain its position during and after the repeated times when medical personnel manipulates the patient's position during medical and surgical treatments. The cap 10 will provide the proper position and contact of sensors 52 for acquiring body sign parameters including: body temperature; electrocardiogram (ECG); respiratory rate (RR) and End Tidal Carbon Dioxide (ETCO2); heart rate (HR); oxygen saturation (SpO2); photoplethysmography (PPG); blood glucose (BG); carbon monoxide level (SpCO); blood pressure (BP); and hydration levels (HL).

About the outer surface 16 and functionally positioned at the forehead region of the wearer's head the display 20 may further be formed a graphical interface for providing direct readout of various body sign through viewing a navigation display.

While various types of body vital sign sensors are currently in use, and it would be obvious to one skilled in the relevant art, in light of the present disclosure, that the specific type of sensor should not form a limitation on the overall functions and features of the present invention. Additionally, it is envisioned that the use of physical tracking of location or position, such as through GPS or other means, may be incorporated for healthcare, military, industrial and consumer markets.

The shell component 14 preferably will provide insulating properties, and may include an insulating filling. However, the material of the shell component is anticipated as being thicker than 1 mm and less than 2 mm thick and adapted for positioning over both lateral side portions of the head. This shell is of a thickness suitable for maintaining the patient's head temperature within euthermic range.

As additionally anticipated, an additional insulating component 19 lining a portion of the inner surface 12. Also illustrated throughout the Figures, the cap 10 will preferably cover below the midpoint of the external auditory meatus bilaterally in addition to the rear portion of the head and upper neck region. The material covering the head has been designed to be in contact with the head in all covered areas so as to prevent a signification amount of air space between the head and the inner material covering the head. To accomplish this, the shell component is made from a pattern cut that is asymmetric from a section of the covering unit adapted for covering the front of the head and a section of the covering unit adapted for covering the rear of the head covering unit, such that the pattern cut has a concave pattern so as to emulate the shape of the front and rear of the head to prohibit the head covering unit from coming off of the head during surgery. Additionally, a number of separate insulating panels, namely a pair of side panels 22 flanking a central panel 24. In such a construction each of the panels 22, 24 may be adjustably fitted about a wearer's head by an adjustable stretch joint 26 positioned between the panels 22, 24 and along their intersections.

The surgical cover 10 insulates a greater portion of the patient's head along approximately the central third, the anterior and the posterior portions. As also illustrated, the surgical cap 10 preferably covers below the midpoint of the external auditory meatus bilaterally in addition to the rear portion of the head and the upper neck region. The inner material that covers the head is designed to be in direct contact with the head to prevent the adverse effects a surgical cap having air gaps has on patient hypothermia. The direct contact is accomplished by means of a shell component made from a pattern cut asymmetrically from a section of the covering unit adapted to cover the front of the head and from a section of the covering unit adapted to cover the rear of the head. The pattern cut is concave to emulate the shape of the front and the rear of a head; it prohibits the surgical cap 10 from falling off during surgery. The pattern forms a gap less than ¾ inch, preferably less than ½ inch and most preferably less than ¼ inch.

It is additionally contemplated that the surgical cap 10 include material that comprises a temperature regulating microfiber. The enclosed cap may further incorporate a chin strap 30 attached to the lower right and the lower left aspects of the surgical cover 10.

It is envisioned that the cap 10 is manufactured in various sizes, e.g., the standard sizes that include extra-small, small, medium, large, extra-large and the like. For a more efficient fit, the surgical cap 10 may comprise the various standard sizes for different age ranges. Additionally, an adjustment or a take-up mechanism may be used to ensure a close-fit over the patient's head without pressing on the patient's head. The surgical cap 10 laterally grips below the patient's external auditory meatus. Finally, it is envisioned that the material used in the head covering unit does not emit sparks nor is it static conductive. It may even be made of a fire-retardant material. It is envisioned that the head covering unit may include attached pouches suitable for the placement of therapeutic or service elements necessary for the functions of the cap, including pouches of heating or cooling materials; hemostatic materials to control bleeding from head wounds; batteries, and diagnostic and analytic units supporting the functions of the vital sign monitors.

Figure 2:
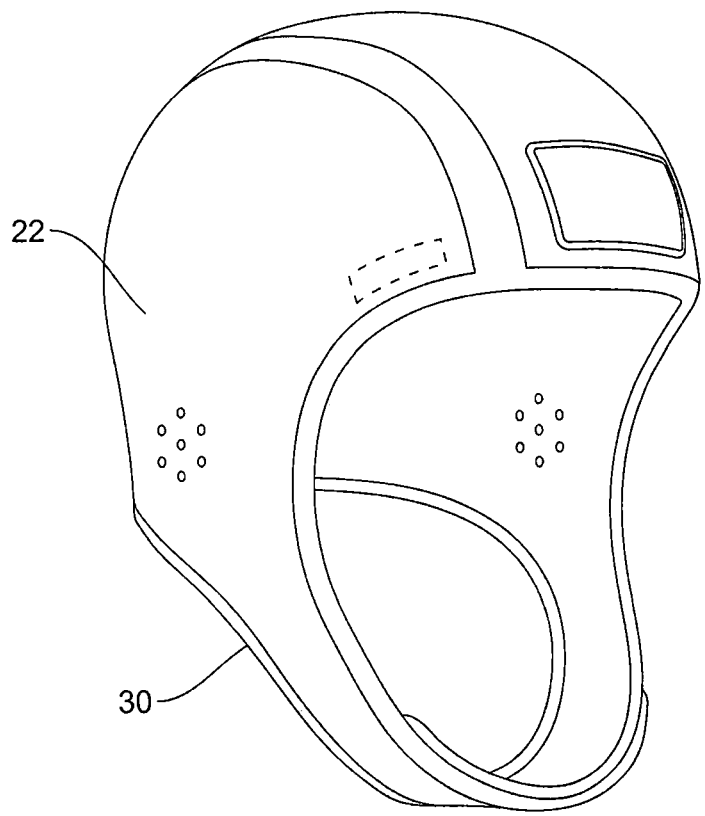
FIG. 2 is a front perspective view of a Surgical Cap to Control Patient Body Temperature according to a first alternate embodiment of the present invention incorporating a securement strap.

FIG. 2 further illustrated that an example of the disclosed invention can be made from a pattern cut that includes a chinstrap 30 that may be provided attached to or extending from each side panel 22 across the opening 16 and at the lower edge 18. The chinstrap 30 is intended to provide additional protection for the prevention of maintaining said head covering on the patient's head during surgery.

2. Operation of the Preferred Embodiment

Figure 3:
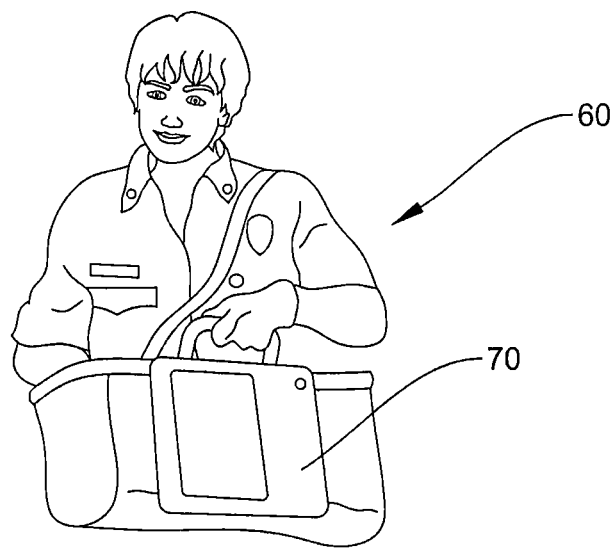
FIG. 3 shows the display screen 20 the present invention for use as a graphical user interface for showing core body vitals of a patient in operative communication with various monitors and lifesaving devices such as a defibrillator.
Figure 4:
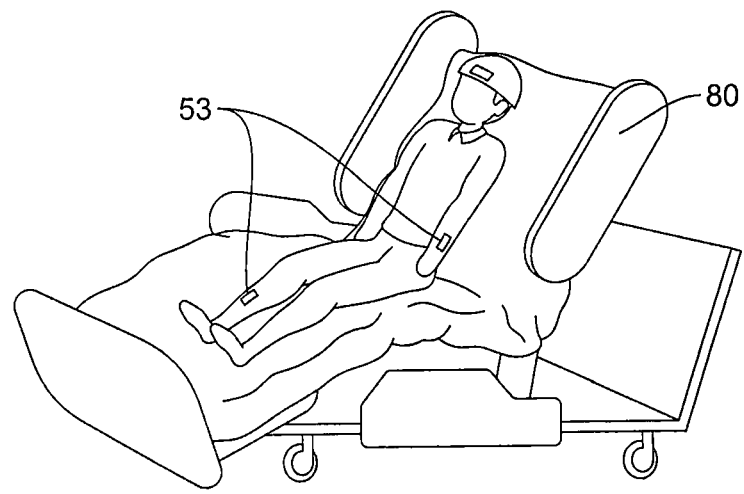
FIG. 4 shows the display screen 20 the present invention for use as a graphical user interface for showing core body vitals of a patient in operative communication with a smart hospital bed.
Figure 5:
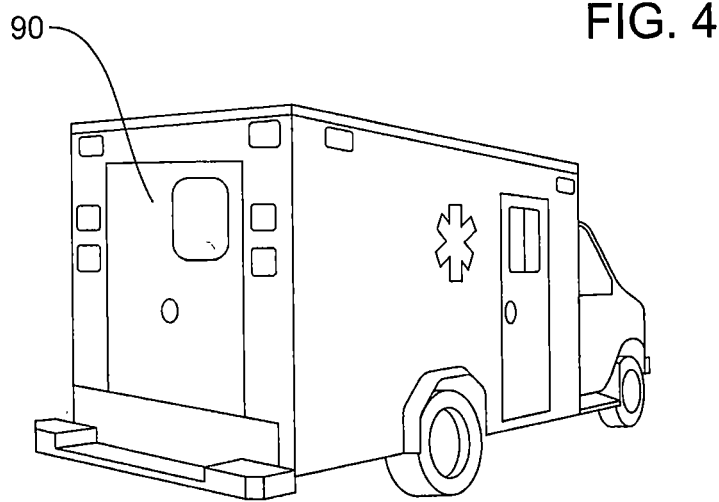
FIG. 5 shows the display screen 20 the present invention for use as a graphical user interface for showing core body vitals of a patient in operative communication with an emergency medical transport vehicle.

In operation, the present invention the covering unit 10 is anticipated for use in maintaining the head temperature and core body temperature within euthermic range for a user in the event of an accident or emergency while on the water. The covering unit 10 is closely fitted to the head 70 and maintains a close proximity. The head covering 10 provides further additional insulation at least a portion of a user's head while being donned. The covering unit 10 is made such as to grippingly engage below the wearer's external auditory meatus bilaterally and conform closely to the user's head. The display screen 20 provides a graphical user interface for showing core body vitals of a patient connected to defibrillators 70 (FIG. 3), smart hospital beds 80 (FIG. 4), smart ambulances 90 (FIG. 5) or similar other medical equipment. The display screen 20 may show, but not be limited too, various vital sign parameters including: body temperature; electrocardiogram (ECG); respiratory rate (RR) and End Tidal Carbon Dioxide (ETCO2); heart rate (HR); oxygen saturation (SpO2); photoplethysmography (PPG); blood glucose (BG); carbon monoxide level (SpCO); blood pressure (BP); and hydration levels (HL). An additional inclusion of a GPS tracking or physical location positioning sensors for may be further incorporated and adapted for healthcare, military, industrial and consumer markets. Further, the display screen may be combined with a number of products and made interactive in order to provide alerts, status or patient care instructions in visual or audible manner.

The teachings of the present invention embodies a number of benefits and improvements. A reduction in the form factor may be obtained with the cumbersome nature of the current defibrillators, reducing the size by a third or more of most current units on the market. Its use also allows a physician, nurse, EMT, or health technician to see the core vitals while they are working and looking at the patient. The screens on the top of current defibrillators are challenging to view. Additionally, value may be provided in allowing display of core vitals in real time on a patient that can be moved around without having to move along with them a large side unit monitoring these vitals.

Use of the present invention incorporating a communication interactive display screen may be combined with a number of products. These include, inter alia, Defibrillators, AEDs, Temperature Management devices, Automated CPR systems, Ventilators, Wearable Defibrillators, IPR Therapy devices, Fluid Resuscitation apparatus and accessories for such devices. The present invention further may be implemented in conjunction with EMS and Fire, Hospital, Public Safety, Military, Homeland Security or Alternate Care markets.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way. Any unintended embracement of such subject matter is hereby disclaimed.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. A method to maintain the euthermic state, said method comprises the steps:
   providing a head covering unit to maintain a user's optimal body temperature, said head covering unit adapted to closely fit the contours of a user's head and forming a grip said user's head in a manner that impedes said covering unit from falling off said user's head during surgery and incorporating a user interface display formed within or attached to head covering unit in a position and location to be visually accessible from an outer surface by a medical care giver;
   locating the display at a position that corresponds generally along the centerline of a wearer's head from front to back; and
   placing one or more monitoring sensors in communication with a patient's body and in operative communication wirelessly with the user interface display;
   displaying information obtained from said one or more monitoring sensors discernable at said user interface display; and
   communicating medical information on the vital signs display mechanism in a visual or audible manner;
   wherein said communicating medical information is selected from a group consisting of: alerts; status; and patient care instructions.

2. The method according to claim 1, wherein said covering is made such as to bilaterally grip below the wearer's external auditory meatus and to conform closely to said user's head.

3. The method according to claim 2, further comprising the step of insulating a greater portion on the anterior of said user's head with insulation as compared to the rest of said head.

4. The method according to claim 3, wherein the portions of said user's head that is insulated are the portions along approximately the central third, the anterior and the posterior of said head.

5. The method of claim 1, wherein said head covering unit further comprises:
   a shell component made from a flexible material that can expand to fit different sized heads and having an inner surface opposite the outer surface; and
   an insulative component, said insulative component lines a portion of said inner surface.

6. The method of claim 1, wherein said one or more monitoring sensors comprises at least one vital signs sensor.

7. The method of claim 5, wherein said insulative component is selected from the group comprising a ceramic fiber material, a phase change material and a synthetic microfiber.

8. The method of claim 1, wherein the position is anterior to a coronal plane of the head covering unit.

* * * * *